United States Patent [19]

Cook et al.

[11] Patent Number: 5,118,841

[45] Date of Patent: Jun. 2, 1992

[54] PROCESS FOR PREPARATION OF CYCLOHEXANEDICARBOXYLIC ACID

[75] Inventors: Steven L. Cook, Kingsport; Gether Irick, Jr., Gray; Crispen S. Moorehouse, Kingsport, all of Tenn.

[73] Assignee: Eastman Kodak Company, Rochester, N.Y.

[21] Appl. No.: 760,680

[22] Filed: Sep. 16, 1991

Related U.S. Application Data

[63] Continuation-in-part of Ser. No. 588,787, Sep. 27, 1990, abandoned.

[51] Int. Cl.$^5$ ............................................. C07C 61/09
[52] U.S. Cl. ...................................................... 562/509
[58] Field of Search .......................................... 562/509

[56] References Cited

U.S. PATENT DOCUMENTS

| | | | |
|---|---|---|---|
| 2,828,335 | 3/1958 | Ferstandig | 562/509 |
| 3,326,972 | 6/1967 | Schenk | 562/509 |
| 3,444,237 | 5/1969 | Jaffe | 562/509 |
| 3,607,917 | 9/1971 | Buls | 562/509 |

OTHER PUBLICATIONS

Groggins, "Unit Processes in Organic Synthesis", 5th Ed., pp. 555–560, 574–583 and 608–612 (1958).
"Kirk–Othmer Encyclopedia of Chemical Technology," 2nd Ed., vol. 6, pp. 510–511 (1965).

*Primary Examiner*—Michael L. Shippen
*Attorney, Agent, or Firm*—Charles R. Martin; William P. Heath, Jr.

[57] ABSTRACT

A process for preparation of 1,3- or 1,4-cyclohexanedicarboxylic acid comprising (A) continuously preparing a solution comprised of the disodium salt of terephthalic acid or isophthalic acid and water, (B) continuously preparing the disodium salt of 1,3- or 1,4-cyclohexanedicarboxylic acid by continuous contacting the solution with hydrogen and the combination of ruthenium metal and a carbon support in a packed column, (C) continuously preparing 1,3- or 1,4-cyclohexanedicarboxylic acid by continuously contacting the disodium salt of 1,3- or 1,4-cyclohexanedicarboxylic acid with sulfuric acid or hydrochloric acid, and (D) continuously recovering the 1,3- or 1,4-cyclohexanedicarboxylic acid by continuous crystallization of the 1,3- or 1,4-cyclohexanedicarboxylic acid.

2 Claims, No Drawings

PROCESS FOR PREPARATION OF CYCLOHEXANEDICARBOXYLIC ACID

This application is a continuation in part of Ser. No. 07/588,787, filed Sep. 27, 1990, now abandoned.

This invention relates to a continuous process for preparation of 1,3- or 1,4-cyclohexanedicarboxylic acid.

It is well known in the art that 1,3- and 1,4-cyclohexanedicarboxylic acid can be prepared from terephthalic acid and isophthalic acid by preparing a aqueous solution of the disodium salt of terephthalic acid or isophthalic acid, reducing the aromatic ring using a ruthenium catalyst, preparing the acid form by contacting the disodium salt with sulfuric acid and recovering the cyclohexanedicarboxylic acid by crystallization. Typical of this art is U.S. Pat. Nos. 3,444,237 and 2,838,335.

We have now discovered a process which results in a very high yield of cyclohexanedicarboxylic acid. In the process of this invention the yield of cyclohexanedicarboxylic acid is at least 85% preferably 90% and most preferably 95%. Broadly, the process of our invention can be described as a process for preparation of 1,3- or 1,4-cyclohexanedicarboxylic acid comprising (A) continuously preparing a solution which has a pH in the range of 7 to 13, a temperature in the range of 20° to 100° and is comprised of 0.5 to 30.0 weight percent of the disodium salt of terephthalic acid or isophthalic acid and 99.5 to 70.0 weight percent water, (B) continuously preparing the disodium salt of 1,3- or 1,4-cyclohexanedicarboxylic acid by continuous contacting the solution with a combination of ruthenium metal and a carbon support in a packed column at a pressure in the range of 100 psig to 2000 psig and a temperature in the range of 20° to 200° C., (C) continuously preparing 1,3- or 1,4-cyclohexanedicarboxylic acid by continuously contacting the disodium salt of 1,3- or 1,4-cyclohexanedicarboxylic acid with sulfuric acid or hydrochloric acid at pressure in the range of atmospheric to 40 psig, and (D) continuously recovering the 1,3- or 1,4-cyclohexanedicarboxylic acid by continuous crystallization of the 1,3- or 1,4-cyclohexanedicarboxylic acid in less than 60 minutes, at a temperature in the range of 130° to 20° C.

In the first step of the invention, an aqueous solution of the disodium salt of terephthalic acid or isophthalic acid is prepared. Preferably the solution is formed by combining terephthalic acid or isophthalic acid with an aqueous solution of sodium hydroxide. The sodium hydroxide and terephthalic acid or isophthalic acid reacts to form the corresponding disodium salt in accordance with well known chemistry. This step can be practiced in commercial equipment well known in the art. Preferably two stirred vessels in series are used because pH can most effectively be used to control the final amount of sodium hydroxide in a vary precise manner.

During the first step, the pH is maintained in the range of 7 to 13, preferably 9 to 11, by adding additional water using conventional means. The temperature is maintained in the range of 20° to 100°, preferably 40° to 90° C.

The amount of disodium salt in the solution can vary from 0.5 to 30.0, preferably 10 to 18, weight percent, based on the weight of the water and disodium salt being 100%. The amount of disodium salt depends on whether the disodium salt of isophthalic acid or terephthalic acid is desired. If isophthalic acid is used, the amount of disodium salt is preferably around 16% due to processing conditions required for the reduced product. If terephthalic acid is used, the amount of disodium salt is preferably around 12% due to solubility limitations.

After the solution of water and disodium salt of terephthalic acid or isophthalic acid is prepared in the first step, the disodium salt of 1,3- or 1,4-cyclohexanedicarboxylic acid is prepared in the second step by reducing the aromatic ring by continuously contacting the solution with hydrogen and a combination of ruthenium metal and a carbon support in a packed column.

The type of packed column is not particularly important as long as the column functions as a fixed bed such that the liquid reactant passes over the catalyst to provide good gas/liquid/solid mass transfer conditions.

Preferably hydrogen and the solution from the first step are introduced into the top of the packed column and the solution descends under the influence of gravity through the column in accordance with so-called "trickle bed" technology.

Packed columns of the type well known in the art are suitable for conducting this step. Preferably two columns are used in series because the crush strength of most carbon catalyst supports limits the bed height.

The pressure in the packed column is in the range of 100 to 2000 psig, preferably 1500 to 2000 psig.

The temperature in the packed column is in the range of 200° to 200° C.

The combination of ruthenium metal and a carbon support is well known in the art and is described in Sci. Repts. Moscow State University., No. 6, 347–52.

In the third step, 1,3- or 1,4-cyclohexanedicarboxylic acid is prepared by continuously contacting the disodium salt of 1,3- or 1,4-cyclohexanedicarboxylic acid with sulfuric acid or hydrochloric acid.

This step can be conducted in standard stirred vessels well known in the art. Typically, the aqueous solution containing 1,4- or 1,3-cyclohexanedicarboxylic acid resulting from the second step is continuously introduced into a stirred vessel along with sulfuric acid. The pressure is maintained in the range of atmosphere to 40 psig. The temperature is maintained at least 80° C.

Preferably two vessels are used in series for the third step because pH can be used to control the final amount of sulfuric acid in a very precise manner. A final pH of 2.8 is most preferred in the case of 1,4-cyclohexanedicarboxylic acid, while a pH of 2.6 is most preferred in the case of 1,3-cyclohexanedicarboxylic acid.

In the fourth step 1,3- or 1,4-cyclohexanedicarboxylic acid is continuously recovered by crystallization of the 1,3- or 1,4-cyclohexanedicarboxylic acid. This step is performed in conventional equipment such as a continuously circulated crystallizer.

The temperature is in the range of 130° to 20° C., preferably 130° to 65° C. The pressure is in the range of 1.5 to 0.1 psig.

We claim:

1. A process for preparation of 1,3- or 1,4-cyclohexanedicarboxylic acid comprising (A) continuously preparing a solution which has a pH in the range of 7 to 13, a temperature in the range of 20° to 100° and is comprised of 0.5 to 30.0 weight percent of the disodium salt of terephthalic acid or isophthalic acid and 99.5 to 70.0 weight percent water,
(B) continuously preparing the disodium salt of 1,3- or 1,4-cyclohexanedicarboxylic acid by continuous contacting the solution with hydrogen and the combination of ruthenium metal and a carbon support in a packed column at a pressure in the range of 100 psig to 2000 psig and a temperature in the range of 20° to 200° C.,
(C) continuously preparing 1,3 or 1,4 cyclohexanedicarboxylic acid by continuously contacting the disodium salt of 1,3- or 1,4- cyclohexanedicarboxylic acid with sulfuric acid or hydrochloric acid at a pressure in the range of atmospheric to 40 psig, and
(D) continuously recovering the 1,3- or 1,4-cyclohexanedicarboxylic acid by continuous crystallization of the 1,3- or 1,4-cyclohexanedicarboxylic acid at a temperature in the range of 130° to 20° C. and a pressure in the range of 15 to 0.1 psig.

2. A process for preparation of 1,3- or 1,4-cyclohexanedicarboxylic acid comprising (A) continuously preparing a solution which has a pH in the range of 9 to 11, a temperature in the range of 40° to 90° and is comprised of 10 to 18 weight percent of the disodium salt of terephthalic acid or isophthalic acid and 90 to 82 weight percent water,
(B) continuously preparing the disodium salt of 1,3- or 1,4-cyclohexanedicarboxylic acid by continuous contacting the solution with hydrogen and the combination of ruthenium metal and a carbon support in a packed column at a pressure in the range of 1500 psig to 2000 psig and a temperature in the range of 20° to 200° C.,
(C) continuously preparing 1,3- or 1,4-cyclohexanedicarboxylic acid by continuously contacting the disodium salt of 1,3- or 1,4-cyclohexanedicarboxylic acid with sulfuric acid or hydrochloric acid at a pressure in the range of atmospheric to 40 psig, and
(D) continuously recovering the 1,3- or 1,4-cyclohexanedicarboxylic acid by continuous crystallization of the 1,3- or 1,4-cyclohexanedicarboxylic acid at a temperature in the range of 120° to 65° C.

* * * * *